United States Patent [19]

Young

[11] Patent Number: 5,055,305

[45] Date of Patent: Oct. 8, 1991

[54] CLEANSING COMPOSITIONS

[75] Inventor: Kenneth Young, Surrey, England

[73] Assignee: Richardson-Vicks, Inc., Shelton, Conn.

[21] Appl. No.: 279,588

[22] Filed: Dec. 2, 1988

[51] Int. Cl.$^5$ .................................................. A61K 9/46
[52] U.S. Cl. ........................................ 424/466; 424/49; 424/50; 424/53; 424/55
[58] Field of Search ................... 424/466, 49, 53, 55, 424/50

[56] References Cited

U.S. PATENT DOCUMENTS

| | | | |
|---|---|---|---|
| 3,372,125 | 3/1968 | Hill | 424/50 X |
| 3,691,016 | 9/1972 | Patel | 424/50 X |
| 3,887,701 | 6/1975 | Nachtigal | 424/452 X |
| 3,911,104 | 10/1975 | Harrison | 424/52 |
| 3,946,108 | 3/1976 | Tomlinson et al. | 424/49 |
| 3,962,107 | 6/1976 | Levin et al. | 424/466 X |
| 3,982,892 | 9/1976 | Gray | 8/111 |
| 4,155,868 | 5/1979 | Kaplan et al. | 252/95 |
| 4,355,022 | 10/1982 | Rabussay | 424/50 X |
| 4,518,520 | 5/1985 | Eoga | 424/78 X |
| 4,770,666 | 9/1988 | Clauss | 8/111 |

FOREIGN PATENT DOCUMENTS

| | | |
|---|---|---|
| 0133354 | 2/1985 | European Pat. Off. . |
| 0149308 | 7/1985 | European Pat. Off. . |
| 0151203 | 8/1985 | European Pat. Off. . |
| 0253772 | 1/1988 | European Pat. Off. . |
| 1261316 | 1/1972 | United Kingdom . |
| 1292482 | 10/1972 | United Kingdom . |
| 1483501 | 8/1977 | United Kingdom . |
| 1527010 | 10/1978 | United Kingdom . |
| 2096162 | 10/1982 | United Kingdom . |

Primary Examiner—Thurman K. Page
Assistant Examiner—Louis A. Piccone
Attorney, Agent, or Firm—David K. Dabbiere; Anthony D. Sabatelli; Douglas C. Mohl

[57] ABSTRACT

Denture cleansing tablet comprising an inorganic persalt bleaching agent, an organic peroxyacid bleach precursor and a solid base material which in the presence of water releases carbon dioxide with effervescence. The composition provides more rapid and efficacious denture cleansing performance and anti-bacterial activity.

9 Claims, No Drawings 5,055,305

CLEANSING COMPOSITIONS

TECHNICAL FIELD

The present invention relates to cleansing compositions in tablet form, and especially to compositions for use in cleansing dentures and the like. In particular, the invention relates to tablet-form compositions having more rapid and efficaceous denture cleansing performance and anti-bacterial activity.

BACKGROUND

Effervescent tablets for cleansing dentures and the like are well known in the art. The aim of a denture cleanser product is to clean the denture as fully and as quickly as possible and especially to remove the accumulation of plaque, mucilageneous and bacterial deposits which collect while the denture is being worn. To wear a denture which has not been completely cleaned of plaque and bacterial deposits is not only unhygienic but can also within a short space of time result in a detrimental effect on the mucous membrane. Moreover bacterial deposits can lead to so-called bacterial corrosion of the plastics material used to produce the denture with consequent color-change and malodor-formation.

Accordingly, the present invention provides a denture cleanser which cleanses more rapidly and which is more efficaceous on plaque, mucilageneous and bacterial deposits than those preparations which are presently known and available on the market.

According to the invention, there is provided a cleansing tablet for dentures and the like comprising an inorganic persalt bleaching agent, an organic peroxyacid bleach precursor and a solid base material having incorporated therein an effervescence producing composition which in the presence of water releases carbon dioxide.

All percentages and ratios herein are by weight of total composition, unless otherwise indicated.

The cleansing tablets of the invention thus comprise three essential components, a bleaching agent, a peroxyacid bleach precursor and an effervescence producing base composition. Each of these will be discussed in turn.

The bleaching agent takes the form of the inorganic persalt and can be selected from any of the well-known bleaching agents known for use in denture cleansers such as the alkali metal and ammonium persulfates, perborates and perphosphates and the alkali metal and alkaline earth metal peroxides. Examples of suitable bleaching agents include potassium, ammonium, sodium and lithium persulfates and perborate mono- and tetrahydrates, sodium pyrophosphate peroxyhydrate and magnesium, calcium, strontium and zinc peroxides. Of these, however, the alkali metal persulfates, perborates and mixtures thereof are highly preferred for use herein.

The amount of bleaching agent in the total composition is generally from about 5 to about 70% preferably from about 10% to about 50%. In the preferred compositions comprising the mixture of alkali metal persulfates and perborates, the overall persulfate:perborate ratio is preferably from about 5:1 to about 1:5, more preferably from about 2:1 to about 1:2.

The compositions herein also contain an organic peroxyacid precursor, which in general terms can be defined as a compound having a titre of at least 1.5 ml of 0.1N sodium thiosulfate in the following peracid formulation test.

A test solution is prepared by dissolving the following materials in 1000 mls distilled water:

| | |
|---|---|
| sodium pyrophosphate ($Na_4P_2O_7 \cdot 10H_2O$) | 2.5 g |
| sodium perborate ($NaBO_2 \cdot H_2O_2 \cdot 3H_2O$) having 10.4% available oxygent | 0.615 g |
| sodium dodecylbenzene sulphonate | 0.5 g |

To this solution at 60° C. an amount of activator is added such that for each atom of available oxygent present one molecular equivalent of activator is introduced.

The mixture obtained by addition of the activator is vigorously stirred and maintained at 60° C. After 5 minutes from addition, a 100 ml portion of the solution is withdrawn and immediately pipetted onto a mixture of 250 g cracked ice and 15 ml glacial acetic acid. Potassium iodide (0.4 g) is then added and the liberated iodine is immediately titrated with 0.1N sodium thiosulphate with starch as indicator until the first disappearance of the blue colour. The amount of sodium thiosulphate solution used in ml is the titre of the bleach activator.

The organic peracid precursors are typically compounds containing one or more acyl groups, which are susceptible to perhydrolysis. The preferred activators are those of the N-acyl or O-acyl compound type containing an acyl radical R—CO wherein R is a hydrocarbon or substituted hydrocarbon group having preferably from about 1 to about 20 carbon atoms. Examples of suitable peracid precursors include.

1) Acyl organoamides of the formula $RCONR_1R_2$, where RCO is carboxylic acyl radical, $R_1$ is an acyl radical and $R_2$ is an organic radical, as disclosed in U.S. Pat No. 3,117,148. Examples of compounds falling under this group include:
   a) N,N - diacetylaniline and N-acetylphthalimide;
   b) N-acylhydantoins, such as N,N'-diacetyl-5,5-dimethylhydantoin;
   c) Polyacylated alkylene diamines, such as N,N,N'N'-tetraacetylethylenediamine (TAED) and the corresponding methylenediamine (TAMD) and hexamethylenediamine (TAHD) derivatives, as disclosed in GB-A-907,356, GB-A-907,357 and GB-A-907,358;
   d) Acylated glycolurils, such as tetraacetylglycoluril, as disclosed in GB-A-1,246,338, GB-A-1,246,339 and GB-A- 1,247,429.

2) Acylated sulphonamides, such as N-methyl-N-benzoyl-menthane sulphonamide and N-phenyl-N-acetyl menthane sulphonamide, as disclosed in GB-A-3,183,266.

3) Carboxylic esters as disclosed in GB-A-836,988, GB-A-963,135 and GB-A-1,147,871. Examples of compounds of this type include phenyl acetate, sodium acetoxy benzene sulphonate, trichloroethylacetate, sorbitol hexaacetate, fructose pentaacetate, p-nitrobenzaldehyde diacetate, isopropeneyl acetate, acetyl aceto hydroxamic acid, and acetyl salicylic acid. Other examples are esters of a phenol or substituted phenol with an alpha-chlorinated lower aliphatic carboxylic acid, such as chloroacetylphenol and chloroacetylsalicylic acid, as disclosed in U.S. Pat. No. 3,130,165.

4) Carboxylic esters having the general formula Ac L wherein Ac is the acyl moiety of an organic carboxylic acid comprising an optionally subsituted, linear or branched $C_6-C_{20}$ alkyl or alkenyl moiety or a $C_6-C_{20}$ alkyl-substituted aryl moiety and L is a leaving group, the conjugate acid of which has a pKa in the range from 4 to 13, for example oxybenzenesulfonate or oxybenzoate. Preferred compounds of this type are those wherein:

a) Ac is $R_3$—CO and $R_3$ is a linear or branched alkyl group containing from 6 to 20, preferably 6 to 12, more preferably 7 to 9 carbon atoms and wherein the longest linear alkyl chain extending from and including the carbonyl carbon contains from 5 to 18, preferably 5 to 10 carbon atoms, $R_3$ optionally being substituted (preferably alpha to the carbonyl moiety) by Cl, Br, $OCH_3$ or $OC_2H_5$. Examples of this class of material include sodium 3,5,5,-trimethylhexanoyloxybenzene sulfonate, sodium 3,5,5-trimethylhexanoyloxybenzoate, sodium 2-ethylhexanoyl oxybenzenesulfonate, sodium nonanoyl oxybenzene sulfonate and sodium octanoyl oxybenzenesulfonate, the acyloxy group in each instance preferably being p-subsituted;

b) Ac has the formula $R_3(AO)_mXA$ wherein $R_3$ is a linear or branched alkyl or alkylaryl group containing from 6 to 20, preferably from 6 to 15 carbon atoms in the alkyl moiety, $R_3$ being optionally subsituted by Cl, Br, $OCH_3$ or $OC_2H_5$, AO is oxyethylene or oxypropylene, m is from 0 to 100, X is O $NR_4$ or CO—$NR_4$, and A is CO, CO—CO, $R_5$—CO, CO—$R_5$—CO or CO—$NR_4$—$R_5$—CO wherein $R_4$ is $C_1-C_4$ alkyl and $R_5$ is alkylene, alkenylene, arylene or alkarylene containing from 1 to 8 carbon atoms in the alkylene or alkenylene moiety. Bleach activator compounds of this type include carbonic acid derivatives of the formula $R_3(AO)_mOCOL$, succinic acid derivatives of the formula $R_3OCO(CH_2)_2COL$, glycollic acid derivatives of the formula $R_3OCH_2COL$, hydroxypropionic acid derivatives of the formula $R_3OCH_2CH_2COL$, oxalic acid derivatives of the formula $R_3OCOCOL$, maleic and fumaric acid derivatives of the formula $R_3OCOCH=CHCOL$, acyl aminocaproic acid derivatives of the formula $R_3CONR_1(CH_2)_6COL$, acyl glycine derivatives of the formula $R_3CONR_1CH_2COL$, and amino-6-oxocaproic acid derivatives of the formula $R_3N(R_1)CO(CH_2)_4COL$. In the above, m is preferably from 0 to 10, and $R_3$ is preferably $C_6-C_{12}$, more preferably $C_6-C_{10}$ alkyl when m is zero and $C_9-C_{15}$ when m is non-zero. The leaving group L is as defined above.

5) Acyl cyanurates, such as triacetyl- or tribenzoyl-cyanurates, as disclosed in U.S. Pat. No. 3,332,882.

6) Optionally substituted anhydrides of benzoic or phthalic acid, for example benzoic anhydride, m-chlorobenzoic anydride and phthalic anhydride.

Of all the above, preferred are organic peracid precursors of types 1(c) and 4(a).

The level of peroxyacid bleach precursor by weight of the total composition is preferably from about 0.1% to about 10%, more preferably from about 0.5% to about 5%.

The effervescent solid base material of the compositions herein preferably comprises a combination of at least one alkali metal carbonate or bi-carbonate, such as sodium bicarbonate, sodium carbonate, sodium sesquicarbonate, potassium carbonate, potassium bicarbonate, or mixtures thereof, in admixture with at least one non-toxic, physiologically-acceptable organic acid, such as tartaric, fumaric, citric, malic, maleic, gluconic, succinic, salicylic, adipic or sulphamic acid, sodium fumarate, sodium or potassium acid phosphates, betaine hydrochloride or mixtures thereof. These effervescent bases produce a vigorous effervescence when in contact with water. The (bi)carbonate components generally comprise from about 5% to about 65%, preferably from about 25% to 55% of the total tablet; the acid components generally comprise from about 5% to about 50%, preferably from about 20% to about 40% of the total tablet.

In preferred embodiments, the solid base material comprises two or more component phases having differing pH in aqueous medium, at least one of the component phases having an acidic pH. In such compositions, the inorganic bleaching agent preferably comprises an alkali metal persulfate and the acidic phase incorporates therein the organic peroxyacid bleach precursor and at least a portion, preferably from about 10% to about 40%, more preferably from about 15% to about 30% of the alkali metal persulfate.

In highly preferred embodiments, the solid base material also comprises at least one phase having an alkaline pH. In such compositions, the inorganic bleaching agent preferably comprises both an alkali metal persulfate and an alkali metal perborate, the acidic phase incorporating therein the organic peroxyacid bleach precursor and at least a portion, preferably from about 10% to about 40%, more preferably from about 15% to about 30% of the alkali metal persulfate, and the alkaline phase incorporating therein the alkali metal perborate.

For optimum antiplaque and antibacterial performance, the cleansing tablet is preferably designed in such a way that the alkaline phase dissolves or disperses in water more slowly or later than the acidic phase in order to provide, on placing the tablet in water, an initial pH in the acidic range, preferably from about 2 to about 6.5 and especially from about 3 to about 5. Moreover, it is preferred that the alkaline phase be present in sufficient excess of the acidic phase in order to shift, upon completion of effervescence, the pH of the aqueous medium into the alkaline range, preferably to a pH of from about 7.5 to about 9. The initial acidic pH should be maintained for a time from about 30 seconds to about 3 hours, preferably from about 1 minute to about 60 minutes and especially from about 12 to about 30 minutes.

The slower dissolution rate of the alkaline phase compared with the acidic phase can be achieved in various ways, for example by the use of alkaline salts or compounds which are inherently sparingly or slowly soluble such as anhydrous sodium carbonate, calcium carbonate, calcium hydroxide, magnesium oxide, or magnesium hydroxide carbonate; or by converting at least a portion of the alkaline phase into a state of slower dissolution rate, for example by melting some of the alkaline phase components to form melt agglomerates followed by comminution to the desired particle size, or by compressing the alkaline phase components with a filler which has a slow dissolution rate such as anhydrous sodium sulfate and slowly water-soluble polymers, for example, proteins, cellulose ethers, cellulose esters, polyvinyl alcohol, alginic acid esters, vegetable fatty acid glycerides and other polymers having a colloidal or pseudo-colloidal character. Moreover, the relative rate of dissolution of the alkaline and acidic phases can be additionally controlled by appropriate formulation and distribution of the effervescent components of the solid base material. In particular, the acidic phase, at least, should incorporate both components of the carbonate or bicarbonate/acid effervescent couple and the effervescence factor of the acidic phase (i.e. the percentage of the phase represented by the least significant of the (bi)carbonate or acid components, measured on a stoichiometric basis) should be greater than that of the alkaline phase and preferably should be greater by a factor of at least 2, and more preferably at least 5. The level of (bi)carbonate and acid components in the acid phase both generally lie in the range from about 10% to about 50% by weight thereof, and preferably from about 20% to about 40% thereof. In highly preferred compositions, the alkaline phase contains a proportion of carbonate or bicarbonate (generally from about 5% to about 40%, preferably from about 10% to about 30% thereof) but is substantially free of any acidic component so that the effervescence factor of the alkaline phase as defined herein is zero.

The compositions of the invention can be in the form of monolayer tablets or can comprise two or more discrete layers. In the case of monolayer tablet, the alkaline and acidic phases are compressed, together with other optional constituents, to a tablet form using, for example, 1-5% by weight; referred to the total tablet composition, of polyvinylpyrrolidone, poly(oxyethylene) of molecular weight 20,000 to 500,000, polyethyleneglycols of molecular weight of from about 1000 to about 50,000 or Carbowax having a molecular weight of from 4000 to 20,000 as binder.

In the case of multilayer tablets, preferably at least one layer comprises the acidic phase and at least one other layer comprises the alkaline phase. The overall ratio of acidic to alkaline phase in the compositions of the invention, both monolayer and multilayer, is preferably from about 10:1 to about 1:20, more preferably from about 2:1 to about 1:5 and especially from about 1:1 to about 1:3. The multilayer tablets can be prepared by precompressing the pregranulated components of a first layer of the multilayer tablet to a pressure of about $10^5$ kPa in a punch and dye tabletting press, adding the pregranulated components of the neighbouring layer with precompression as appropriate and repeating until the components of all layers of the tablet are in the press. The tablet is then given a final compression at about $1.5 \cdot 10^5$ kPa. A binder as described above will normally be present in each of the layers of the multilayer tablet.

The solid base material of the compositions of the invention can be supplemented by other usual components of cleansing tablet formulations, especially surfactants, chelating agents, enzymes, flavor oils such as oils of spearmint, peppermint and wintergreen, dyestuffs, sweeteners, foam depressants such as dimethylpolysiloxanes, foam stabilizers such as the fatty acid sugar esters, preservatives, lubricants such as talc, magnesium stearate, finely divided amorphous pyrogenic silicas, etc. The free moisture content of the final composition is desirably less than about 1% and especially less than about 0.5%.

The surface active agent used in the compositions of the invention can be selected from the many available that are compatible with the other ingredients of the denture cleanser, both in the dry state and in solution. Such materials are believed to improve the effectiveness of the other ingredients of the composition by aiding their penetration into the interdental surfaces. Also, these materials aid in the removal of food debris attached to the teeth. Between 0.1 and 5 percent by weight of the dry composition of a dry powder or granular anionic surface active agent, such as sodium lauryl sulfate, sodium N-lauroylsarcosinate, sodium lauryl sulfoacetate or dioctyl sodium sulfosuccinate or ricinoleyl sodium sulfosuccinate, may, for example, be included in the composition and preferably the surface active agent comprises between 2 and 4 percent of the composition.

Suitable cationic, non-ionic and ampholytic surface active agents include, for example, quaternary ammonium compounds such as cetyltrimethylammonium bromide, condensation products of alkylene oxides such as ethylene or propylene oxide with fatty alcohols, phenols, fatty amines or fatty acid alkanolamides, the fatty acid alkanol amides themselves, esters of long-chained ($C_8$-$C_{22}$) fatty acids with polyalcohols or sugars, for example glycerylmonostearate or saccharosemonolaurate or sorbitolpolyoxyethylenemono-or di-stearate, betaines, sulphobetaines or long-chain alkylaminocarboxylic acids.

Chelating agents beneficially aid cleaning and bleach stability by keeping metal ions, such as calcium, magnesium, and heavy metal cations in solution. Examples of suitable chelating agents include sodium tripolyphosphate, sodium acid pyrophosphate, tetrasodium pyrophosphate, aminopolycarboxylates such as nitrilotriacetic acid and ethylenediamine tetracetic acid and salts thereof, and polyphosphonates and aminopolyphosphonates such as hydroxyethanediphosphonic acid, ethylenediamine tetramethylenephosphonic acid, diethylenetriaminepentamethylenephosphonic acid and salts thereof. The chelating agent selected is not critical except that it must be compatible with the other ingredients of the denture cleanser when in the dry state and in aqueous solution. Advantageously, the chelating agent comprises between 0.1 and 60 percent by weight of the composition and preferably between 0.5 and 30 percent. Phosphonic acid chelating agents, however, preferably comprise from about 0.1 to about 1 percent, preferably from about 0.1% to about 0.5% by weight of composition.

Enzymes suitable for use herein are exemplified by proteases, alkalases, amylases, lipases, dextranases, mutanases, glucanases etc. The enzyme is expediently present in a discrete layer of a multilayer tablet.

The following Examples further describe and demonstrate the preferred embodiments within the scope of the present invention.

EXAMPLES I TO IV

The following are representative two-layer denture cleansing tablets according to the invention. The percentages are by weight of the corresponding layer.

| | I | II | III | IV |
|---|---|---|---|---|
| Acidic Layer | | | | |
| Tartaric Acid | 25 | 22 | 15 | — |
| Citric Acid | — | — | 15 | 20 |
| Sodium Carbonate | 4 | 5 | — | 5 |
| Sulphamic Acid | 10 | 12 | 5 | 14 |
| PEG 20,000 | 4 | 3 | 1 | 3 |
| PVP 40,000 | — | — | 3 | — |
| Sodium Bicarbonate | 24.5 | 23 | 26.4 | 37.2 |
| Potassium Persulfate | 15 | 12 | 16 | 5 |
| Sodium acid Pyrophosphate | 7 | 10 | 8 | 7 |
| Pyrogenic Silica | 2 | 3 | — | 1 |
| Talc | — | — | 2 | — |
| TAED[1] | 7 | — | 6 | — |

|  | I | II | III | IV |
|---|---|---|---|---|
| TMHOS[2] | — | 8 | — | 5 |
| EDTMP[3] | — | — | 1 | 1 |
| Ricinoleylsulfosuccinate | 0.5 | 1 | 0.6 | 0.8 |
| Flavour | 1 | 1 | 1 | 1 |
| Alkaline Layer | | | | |
| Sodium Perborate Monohydrate | 32 | 30 | 10 | 35 |
| Sodium Bicarbonate | 19 | 21 | 17 | 20 |
| EDTA | 3 | 2 | — | — |
| Sodium Tripolyphosphate | 12 | 10 | — | 8 |
| Sodium Pyrophosphate | — | — | 6 | — |
| PEG 20,000 | 2 | 3 | — | — |
| PEO[4] | — | — | — | 3 |
| Potassium Persulfate | 26 | 28 | 30 | 25 |
| Sodium Carbonate | 2 | 2 | 30 | 5 |
| Magnesium Stearate | — | — | — | 2 |
| Pyrogenic Silica | 2 | 2 | — | — |
| $C_{8-12}$ fatty acid glyceride | — | — | 5 | — |
| Dye/Flavour | 2 | 2 | 2 | 2 |

[1]Tetraacetylethylene diamine
[2]Sodium 3,5,5-trimethylhexanoyloxybenzene sulfonate
[3]Ethylenediaminetetramethylenephosphonic acid
[4]Polyoxyethylene - molecular weight 100,000

In Examples I to IV above, the weight ratio of alkaline layer:acidic layer in each instance, is 70:30. The overall tablet weight is 4 g; diameter 25 mm.

The denture cleansing tablets of Examples I to IV display more rapid and efficacious denture cleansing performance and bacterial activity than corresponding compositions which are free of peroxyacid bleach precursor.

What is claimed is:

1. Denture cleansing tablet comprising:
   (a) an inorganic persalt bleaching agent wherein said agent comprises a mixture of alkali metal persulfate and alkali metal perborate bleaching agents;
   (b) an organic peroxyacid bleach precursor; and
   (c) a solid base material having incorporated therein an effervescence producing composition which in the presence of water releases carbon dioxide, and wherein the solid base material comprises two or more component phases having different pH in aqueous medium, at least one phase having an acidic pH and having incorporated therein the organic peroxyacid bleach precursor and at least a portion of the alkali metal persulfate, and at least one other phase having an alkaline pH and having incorporated therein the alkali metal perborate.

2. Cleansing tablet according to claim 1 wherein the alkaline phase dissolves or disperses in water more slowly than or later than the acidic phase in order to provide, on placing the tablet in water, an initial pH in the acidic range.

3. Cleansing tablet according to claim 2 wherein the initial pH is from about 2 to about 6.5 and is maintained within the acid range for from about 30 seconds to about 3 hours.

4. Cleansing tablet according to claim 3 wherein the initial pH is from about 3 to about 5 and is maintained within the acid range for from about 1 minute to about 60 minutes.

5. Cleansing tablet according to claim 4 wherein the alkaline phase is present in sufficient excess of the acidic phase in order to shift, upon completion of effervescence, the pH of the aqueous medium into the alkaline range.

6. Cleansing tablet according to claim 5 wherein the solid base material comprises a (bi)carbonate/acid effervescent couple and wherein at least the acidic phase incorporates both components of the effervescent couple.

7. Cleansing tablet according to claim 6 comprising two or more discrete layers, at least one layer comprising the acid phase and at least one other layer comprising the alkaline phase.

8. Cleansing tablet according to claim 7 wherein the organic peroxyacid bleach precursor is selected from the group consisting of acylated polyalkyldiamines and carboxylic esters having the general formula AcL wherein Ac is the acyl moiety of an organic carboxylic acid comprising an optionally substituted, linear or branched $C_6$-$C_{20}$ alkyl or alkenyl moiety or a $C_6$-$C_{20}$ alkyl-substituted aryl moiety and L is a leaving group, the conjugate acid of which has a pKa in the range from 4 to 13.

9. Cleansing tablet according to claim 1 wherein the organic peroxyacid bleach precursor is selected from carboxylic esters having the general formula AcL wherein Ac is the acyl moiety of an organic carboxylic acid comprising an optionally substituted, linear or branched $C_6$-$C_{20}$ alkyl or alkenyl moiety or a $C_6$-$C_{20}$ alkyl-substituted aryl moiety and L is a leaving group, the conjugate acid of which has a pKa in the range from 4 to 13.

* * * * *